(12) United States Patent
Janka et al.

(10) Patent No.: US 8,717,550 B2
(45) Date of Patent: May 6, 2014

(54) METHOD AND DEVICE FOR DETECTING BIOLOGICAL MATERIAL

(75) Inventors: Kauko Janka, Tampere (FI); Jorma Keskinen, Tampere (FI); Matti Putkiranta, Hameenlinna (FI); Sampo Saari, Tampere (FI); Katja Bengtsson, Mikkeli (FI)

(73) Assignee: Environics Oy, Mikkeli (FI)

( * ) Notice: Subject to any disclaimer, the term of this patent is extended or adjusted under 35 U.S.C. 154(b) by 0 days.

(21) Appl. No.: 13/699,768

(22) PCT Filed: Jun. 7, 2011

(86) PCT No.: PCT/FI2011/050534
§ 371 (c)(1),
(2), (4) Date: Nov. 26, 2012

(87) PCT Pub. No.: WO2011/154605
PCT Pub. Date: Dec. 15, 2011

(65) Prior Publication Data
US 2013/0077087 A1    Mar. 28, 2013

Related U.S. Application Data

(60) Provisional application No. 61/399,122, filed on Jul. 8, 2010.

(30) Foreign Application Priority Data

Jun. 7, 2010    (FI) ...................................... 20105645

(51) Int. Cl.
*G01N 21/00*    (2006.01)

(52) U.S. Cl.
USPC ........................................... 356/73; 356/335

(58) Field of Classification Search
USPC ............ 356/73, 335–343, 39–42; 250/459.1, 250/458.1, 461.1, 462.1, 461.2, 491.2; 435/30, 34; 436/10, 52, 172; 702/22, 702/19, 29, 21, 26; 382/100, 128, 159, 181, 382/190
See application file for complete search history.

(56) References Cited

U.S. PATENT DOCUMENTS

| | | | |
|---|---|---|---|
| 5,895,922 | A | 4/1999 | Ho |
| 5,940,177 | A | 8/1999 | Esser et al. |
| 7,060,992 | B1 | 6/2006 | Barney |
| 2004/0010379 | A1 | 1/2004 | Craig et al. |

FOREIGN PATENT DOCUMENTS

WO    2005/085842    9/2005

*Primary Examiner* — Tri T Ton
(74) *Attorney, Agent, or Firm* — Fildes & Outland, P.C.

(57) ABSTRACT

The invention relates to a method for detecting biological material in an airstream, in which method the airstream is fed with the aid of sampling devices, a light beam is emitted towards the airstream, a fluorescence signal depicting the fluorescence of the particle is created, a scattering signal depicting the scattering of the light of the particle is created, the fluorescence signal and the scattering signal are converted into discrete values, and an alarm value is defined. The discrete values are recorded cumulatively as hit points in an at least 2-dimensional measurement space equipped with selected dimensions, at least one index area is preselected from the measurement space, a cumulative index is calculated at an index frequency from the hit points accumulated on the each preselected index area, and an alarm value, showing the presence of a selected biological material, is defined from the indices by using a preselected criterion.

14 Claims, 3 Drawing Sheets

METHOD AND DEVICE FOR DETECTING BIOLOGICAL MATERIAL

Figure 1:
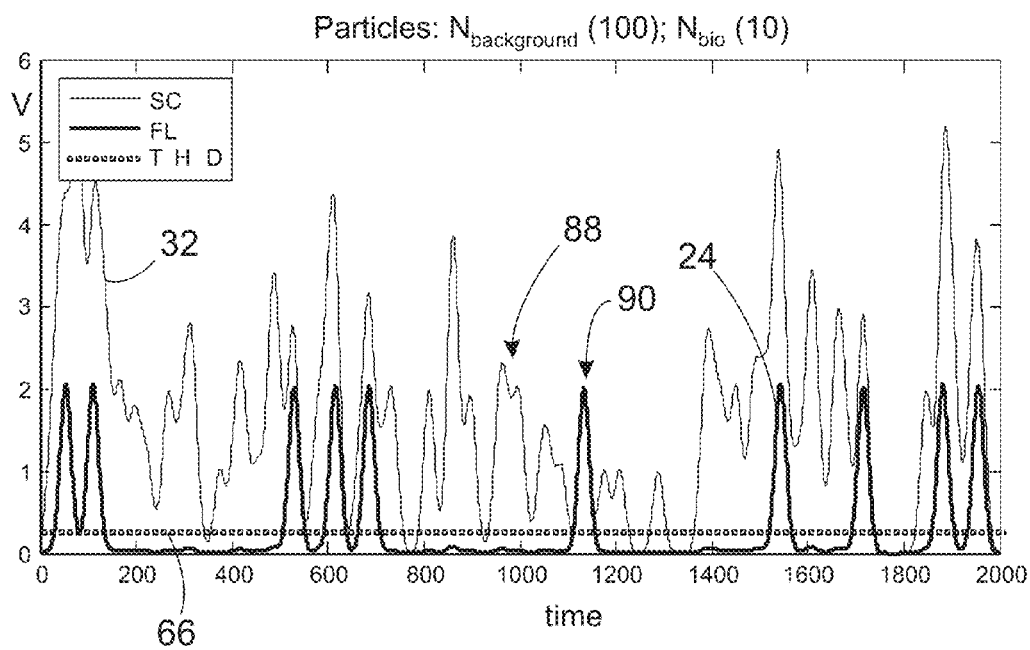

The present invention relates to a method for detecting biological material in an airstream, which airstream contains particles of biological material and/or biologically inert material, in which method the airstream is fed with the aid of sampling devices into a chamber and out of the chamber after sampling, a light beam is emitted towards the airstream by a light source, in order to excite the particles in the airstream, in order to create fluorescence, the fluorescence emitted by each particle struck by the light beam is measured with the aid of first measuring means and a fluorescence signal depicting the fluorescence of the particle is created, the scattered light from each particle struck by the light beam is measured with the aid of second measuring means and a scattering signal depicting the scattering of the light of the particle is created, the fluorescence signal and scattering signal are converted into discrete values at the sampling frequency, and an alarm value is defined on the basis of the discrete values.

The invention also relates to a corresponding device for detecting biological material.

Biological warfare agents are dangerous weapons of mass destruction, which are a significant threat due, for example, to terrorist organizations. Biological warfare agents are often spread as aerosol particles, which are difficult to detect. In this connection, aerosol refers to air and particles floating in it.

The prior art in the detection of warfare agents is represented by patent publication U.S. Pat. No. 5,701,012, which discloses an apparatus exploiting the fluorescence of a biological material. In the apparatus, each particle directed to the device is excited by a laser beam, after which a measuring device is used to measure the fluorescence emitted by the particle. The fluorescence values of every particle are compared one at a time with an internal database, based on which a decision is made as to the biological viability of the particle.

In the device according to the US patent, the decision is made from an individual particle. However, it is demanding and expensive to implement an electronic circuit determining the differentiating and peak values of the fluorescence pulse of an individual particle. In addition, in a situation, in which the air has a high particle content, the so-called coincidence phenomenon becomes probable, thus causing problems in the measurement of individual particles. The signal is then formed from several particles that are simultaneously in the detection chamber. In such a situation, an estimate of the biological viability of an individual particle based on fluorescence may be erroneous, because the fluorescence may not necessarily originate from a single particle.

Also known from the prior art is U.S. Pat. No. 7,738,099 B2, which discloses an apparatus, by means of which the light scattered by the particle, as well as the fluorescence emitted by the particle, can be measured. In this case too, the peak value of each pulse is measured, on the basis of which a possible biological particle is detected. In order to work, such a solution demands a complex electronic section for measuring and analysing the peak heights of the pulses, which operates weakly at large particle contents.

The present invention is intended to create a method for detecting biological material, which is simpler than the prior art. It is also intended to create a device for detecting biological material, which is simpler and better than the prior art. The method and device according to the invention are particularly suitable for detecting/identifying biological particles.

The characteristic features of the method according to the invention are stated in the accompanying Claim 1 and the characteristic features of the device in the accompanying Claim 12.

This intention can be achieved by means of a method for detecting a biological material in an airstream, which contains particles of biological material and/or biologically inert material, in which method the discrete values are recorded cumulatively as hit points in at least a 2-dimensional measurement space equipped with selected dimensions, at least one index area of which measurement space is preselected. A cumulative index is calculated for each preselected index area at regular intervals from the accumulated hit points and an alarm value showing the presence of a selected biological material is defined from the indices using preselected criteria. In the method, the airstream is fed with the aid of sampling means into the chamber and out of the chamber after sampling and a light beam is emitted towards the airstream by a light source, in order to excite the particles in the airstream, in order to create fluorescence. The fluorescence emitted by each particle hit by the light beam is measured with the aid of measuring means and a fluorescence signal depicting the fluorescence of the particle is created and correspondingly the light scattered by each particle hit by the light beam is measured with the aid of second measuring means and a scattering signal depicting the scattering of the light by the particle is created. The fluorescence signal and the scattering signal are converted into discrete values at the sampling frequency for classification and analysis and, on the basis of the discrete values, an alarm level is defined.

The method can be implemented without defining single peak value from the fluorescence and scattering signals, thanks to which the method is extremely simple. This means that the method will tolerate the coincidence phenomenon considerably better than the prior art and even correct measurement errors caused by it.

There are preferably at least two index areas, most preferably at least three of them. The use of more index areas will reduce the inaccuracy and false alarms of the method and device, especially in difficult outdoor conditions, in which chimney gases and other impurities can disturb detection.

The indices are preferably compared, to relative conditions between each index and absolute conditions for at least some of the indices, on the basis of which, when the conditions are met, an alarm is given. The comparison of the indices is simple and fast.

The measurement space is preferably a memory. Thus, the discrete values are recorded in the memory directly as hit points, without unnecessary intermediate stages.

The light beam is preferably emitted using a light source perpendicularly to the airstream. The light source can be arranged to use a constant frequency.

The device is preferably arranged to display the fluorescence signal and scattering signal continuously/at a constant sampling frequency. The processing methods for continuous fluorescence and scattering signals can be applied simply. With continuous displaying, the number of data points corresponding to approximately the correct particle content is obtained for the areas specific to bio particles and background particles. The sampling frequency can be 100 kHz-2 MHz, preferably 300-800 kHz.

According to one embodiment, in an at least 2-dimensional memory the dimensions are the fluorescence of the particles and the light scattered by the particles. These dimensions are obtained directly from the discrete values, without computational operations.

According to a second embodiment, in an at least 2-dimensional memory the dimensions are the light scattered by the particles and the product of the fluorescence of the particles and the arrival of the light scattered by the particles.

The interval of the calculation of the cumulative indices can be 0.1-10 s, preferably 0.8-1.5 s. The amount of data accumulating in the memory will then remain reasonable and calculation can be performed rapidly.

According to one embodiment, the correlations of the discrete values are used in calculating the indices. Thus, when creating a result, the signal values used are multiplied mutually, in such a way that at least the long-term mean value (or so-called DC component) of at least the second signal is eliminated. This elimination can be performed, for example, in a simple and, as such, known manner, by performing so-called high-pass filtering of the signal in question, before multiplying two signals.

According to a second embodiment, the mean product of the discrete values is used in calculating the indices. The results of such processing methods can be easily further arranged as maps for the actual algorithms, or they can be integrated to form easily processable parameters, for example, correlation coefficients, the time integral of the scattering, or the time integral of the fluorescence.

In addition, other derivative values too, calculated from the fluorescence and scatterings signals, can be used in the calculation of the indices. Such derivative values can be the correlation values between the signals, or the mutual ratios of the signals. For example, by dividing the value of the fluorescence signal by the value of the scattering signal a number will be obtained, which depicts the amount of biological material contained in the particles.

According to one embodiment, the analysis means are arranged to form classification maps on the basis of the signals, in order to detect biological material. The interpretation of the classification maps is simple and fast.

When the alarm value exceeds the preselected criterion, the alarm and display means preferably give an alarm. The alarm can be given in three steps, in the following stages: biological material is detected in the airstream, when the alarm level exceeds the preselected criterion, the alarm and display means give an alarm and take samples from the airstream for more detailed analysis.

The intention of the device according to the invention can be achieved by using the device to detect biological material in air, which contains biological material as particles and/or biologically inert material, which device includes classification means and a memory, of which the classification means are arranged to record the discrete values cumulatively as hit points in the memory equipped with at least 2-dimensional selected dimensions. In the device, the analysis means are arranged to calculate an index at an index frequency from the accumulated hit points for each preselected index area, from which indices the analysis means are arranged to define, using a preselected criterion, an alarm value depicting the presence of a selected biological material. In other words, the individual memory locations act as hit-point counters, i.e. the contents of a single memory location are incremented at the sampling frequency. The memory location in question corresponds to the said discrete signal values.

The device further includes sampling means for feeding an airstream into a chamber and leading the airstream out of the chamber after sampling, a light source focussed on the airstream and arranged to emit a beam in order to excite the particles in the airstream in order to create fluorescence, and measuring means for measuring the fluorescence emitted by the particles struck by the beam and for creating a fluorescence signal depicting the fluorescence. The device also includes second measuring means for measuring the light scattered by the particles struck by the light beam and for creating a scattering signal depicting the scattered light, at least one AD converter for sampling the fluorescence signal and the scattering signal as discrete values at the sampling frequency and analysis means for detecting biological material.

The selected dimensions of the device according to the invention can be 10×10-30×30, preferably 15×15-20×20. The device preferably also further includes alarm and display means for issuing an alarm on the basis of the said alarm value.

The alarm and display means are preferably arranged to compare the alarm value with conditions, which conditions comprise the examination of indices determined from the duration of at least two different periods of time.

According to one embodiment, the device includes software means, comprising at least two software timers for determining the two periods of time of different lengths for the examination of the indices.

The implementation of the device according to the invention is economical, as the sampling and recording using the device can be performed without difficult electronics and/or logic, in order to determine the peak values of individual signals or some other variable depicting them, as is the case in devices of the prior art. By means of the device according to the invention, the measurements can be performed in considerably larger sample-flow ranges, without the magnitude of the sample flow affecting the result of the measurement. In other words, the precise and time-consuming measurement and regulation of the device's sample flow is unnecessary.

The sampling frequency of the signals can be varying and even random without affecting the end result, even though both signals fluorescence and scattering are measured essentially simultaneously. The device is therefore easy to implement on both the hardware and software levels.

The device according to the invention, is robust and sensitive in the detection of bio-aerosol particles and with the help of which the detrimental bio-aerosol particles can be constantly monitored and warned off. Its robust construction permits the device to be used in a wide range of conditions.

Figure 3:
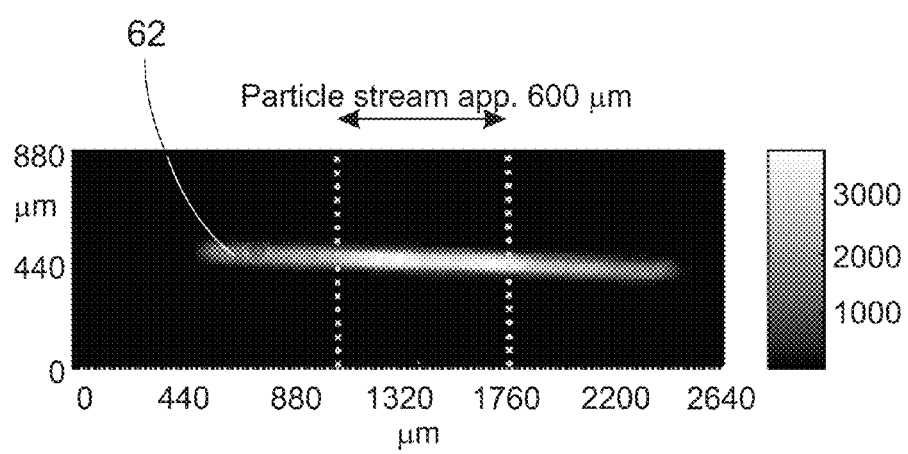
Figure 2:
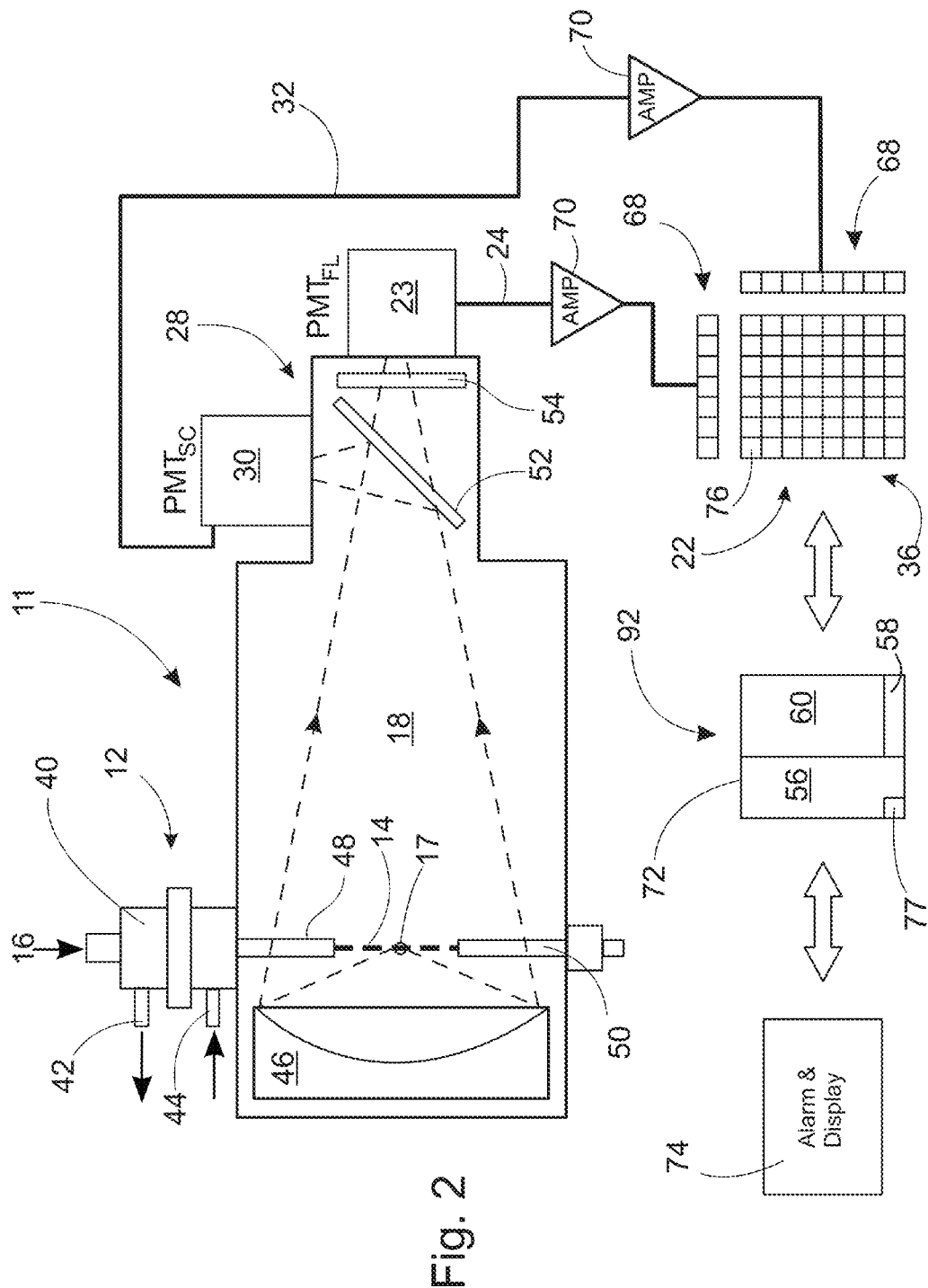
Figure 4:
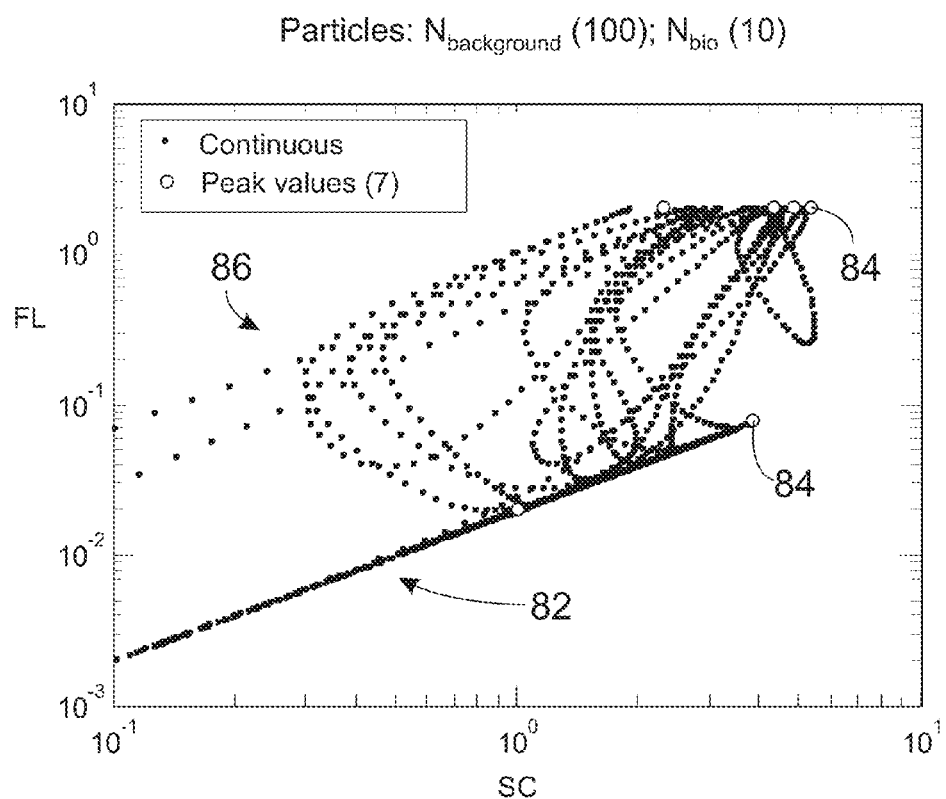
Figure 5:
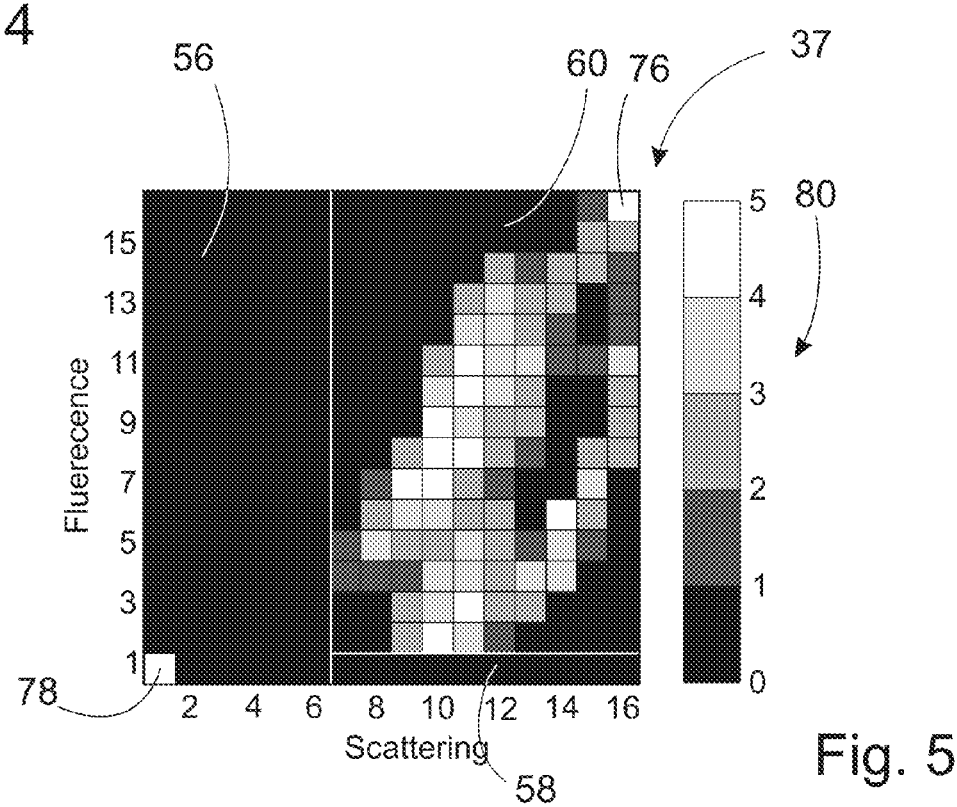

In the following, the invention is described in greater detail with reference to the accompanying drawings depicting some embodiment of the invention, in which FIG. 1 shows the principle of processing in devices of the prior art, with the aid of fluorescence and scattering signals measured from particles, FIG. 2 shows a simple block diagram and schematic image of the device according to the invention, FIG. 3 shows a typical beam profile of the laser beam of the device according to the invention, FIG. 4 shows the peak values and continuous sampling points measured by the device according to the invention in a logarithmic set of fluorescence-scattering co-ordinates, FIG. 5 shows a classification map of the device according to the invention.

FIG. 1 shows a fluorescence signal 24 and scattering signal 32 measured using a device according to the prior art. In both curves, the individual peaks, such as the peak 90, represent individual particles detected by the device. The high scattering peaks have been caused by large particles, whereas the smaller peaks are caused by small particles. The high peak in the fluorescence graph depicts a particle, which has contained a substance with a great deal of fluorescence. Curve SC of the curves shown in FIG. 1 refers to scattering, FL to fluorescence, and THD to the trigger level 66, i.e. the level above which signals are measured. In devices of the prior art, the detection of biological particles is based on the measurement of the peak values of the fluorescence and scattering signals. An individual peak value is assumed to represent an individual biological particle. A peak value is measured only if it exceeds the trigger level 66.

However, a problem in this procedure is that, if the particle content of the air is large, the probability of the so called coincidence phenomenon increases, causing problems in the measurement of individual particles. For example, at the signal peak 88, the signal is formed by several particles that are simultaneously in the detection chamber. However, the measurement of the signal's peak value processes this as only a single peak value. If such a peak is in a fluorescence signal, the estimate of the biological viability of an individual particle may be erroneous, because the fluorescence does not necessarily originate from a single particle. In other words, in a coincidence situation, there can be several particles simultaneously in the detection chamber, so that individual pulses from the particles can no longer be clearly differentiated from each other, but often partly overlap.

FIG. 2 shows one embodiment of the device according to the invention. The device 10 includes a measuring unit 11 containing sampling means, a light source, division means 28, first measurement means 23 and second measurement means 30. The light source is not shown, because the light source 17 runs perpendicularly to the plane of FIG. 2, from the view to the plane or vice versa. Only the light beam 17 is marked. According to the figure, the sampling means 12 can include a concentrator 40, a suction-flow connection 42, and a protective air connection 44, with the aid of which the air sample is processed for measurement. The airstream is first brought to a virtual-impactor-type concentrator 40. In the concentrator 40 is a suction-flow connection 42, which reduces the airstream 16 to a tenth part of the original. At the same time, the strongly rotating suction flow increases the concentration of the larger particles in the airstream 16.

The concentrated sample is directed to a light-tight optical chamber, i.e. the chamber 18, in which the scattering and fluorescence are measured. The airstream 16 to the optical chamber 18 comes from the end of the narrow upper nozzle 48 and is surrounded by clean protective air coming from a protective-air connection 44, so that the chamber will remain clean. The stream of particles 14 travels freely through the optical chamber and ends in the lower nozzle 50, from which it exits. The optical measurement of the particles 14 is made between the upper nozzle 48 and the lower nozzle 50. In the optical chamber, the stream of particles 14 strikes the light beam 17, when scattering light and possibly fluorescence light induced by the light beam arise. The light beam is preferably a diode laser type, the wavelength of which is 405 nm. From now on, the name laser-beam source can also be used for the light source. The laser-beam source can be arranged to use a constant frequency. The laser beam can be a UV laser beam, the power of which can be, for example, 200 mW.

So that the intensity of the light coming from the particles 14 would be sufficient, it is collected at a relatively large solid angle with the aid of an ellipsoid mirror 46 to the photomultiplier tube (PMT), i.e. to the first measuring means 23 and the second measuring means 30, as can be seen from FIG. 2. The collection angle of the ellipsoid mirror 46 can be, for example, ¼ of the solid angle and the optical magnification. There are preferably division means 28 before the photomultiplier tube, which include a dichroidic mirror 52, which reflects the scattering light to the second photomultiplier tube (PMT SC), i.e. to the second measuring means 30. The reflected light can have a wavelength of <440 nm. Longer wavelength light, which can have a wavelength of >440 nm, goes through the dichroidic mirror 52 and continues to travel to photomultiplier tube (PMT FL) measuring fluorescence, i.e. to the first measuring means 23. The first measuring means 23 can be used to measure the fluorescence, for example, from the wavelength band 442-600 nm and the second measuring devices 30 can be used to measure scattering from the wavelength 405 nm. In the first measuring devices 23, there can be, in addition, a high-pass filter 54 belonging to the dividing means 28, which passes through only fluorescing light according to the wavelength >442 nm. Thus, the fluorescence and scattering lights can be separated from each other.

Processing of the laser beam plays an important part in optimizing the performance of the device. The laser beam is shaped into a suitable shape and size, before it is brought into the chamber. First the laser beam is collimated to become parallel by means of a so-called collimator lens. Then the beam is focussed by a cylindrical lens at the particle stream, when a very flat and wide beam profile will be obtained. After the cylindrical lens there are still two gap limiters, which prevent stray radiation from entering the chamber. The means required to shape and collect the laser beam are not shown in the figure, but they can be means widely used in technology. FIG. 3 shows a typical beam profile 62 at the particle stream, the dimensions of which in this embodiment are about 2000× 100 μm. The number of particles striking the beam and the intensity of the laser light are optimized in the shape of the beam.

Further relating to FIG. 2, in addition to the measuring unit 11 the device 10 includes at least one signal amplifier 70, at least one A/D converter 68, classification means 36, analysis means 92, and alarm and display means 74. In the embodiment shown in FIG. 2, there are separate signal amplifiers 70 and A/D converters 68 for both the fluorescence signal 24 and the scattering signal 32.

The classification means 36 of the embodiment shown in FIG. 2 include A/D converters 68 and a memory 22. The device 10 is preferably arranged to display the signals continuously. This means that the fluorescence and scattering signals are measured continuously without examining them individually. In the photomultiplier tubes there are adjustable amplifier voltages (Gain), by means of which their output signals can be amplified. In addition, after the measuring devices 23 and 30 there can be the signal amplifiers 70 according to FIG. 2.

In the embodiment of FIG. 2, a continuous fluorescence signal 24 and scattering signal 32 coming from the measuring devices 23 and 30 are displayed at the sampling frequency as discrete values. The sampling frequency can be 100 kHz-2 MHz, preferably 300-800 kHz. According to a preferred embodiment, the discrete values measured simultaneously receive co-ordinate values on the basis of the magnitude of the measured voltage, on the basis of which an individual hit point is recorded in a measuring space equipped with preselected dimensions. In this embodiment, the term measuring space refers to individual memory locations 76 in the memory 22. One dimension of the measuring space, i.e. a co-ordinate axis of the memory, can be fluorescence and the other scattering. All the signals measured using the measuring devices 23 and 30 are converted into discrete values with the aid of an A/D converter 68 and stored in the memory 22. In the method, the detection of a biological material is performed digitally.

FIG. 4 shows the displayed discrete values of the continuous fluorescence and scattering signals measured in FIG. 1 at the sampling frequency, in a logarithmic graph. In the graph, an individual hit point 86 shows the discrete value of a fluorescence and scattering signal at a specific moment in time. The figure also shows the measured peak values 84. From such a presentation, it can be seen how the base level 82 is formed of background particles. In practice, the graph of FIG. 4 shows the same matter as the graph of FIG. 5, but in FIG. 5 the hit points are related to each other in the figure and the spacing of the axes is different.

The analysis means 92 include an examination frame 72, which consists of at least two index areas delimited on the basis of empirically predefined conditions. In this case, there are three index areas 56, 58, and 60. The index areas are defined according to the properties of the biological particles displayed. At regular intervals, for example, at one-second intervals, the examination frame 72 is used to examine the memory 22, when an index depicting each index area 56, 58, and 60 is calculated for the index areas 56, 58, and 60 with the aid of the hit points accumulated in the memory 22. The indices can be calculated, for example, by the arithmetical sum of the hit points recorded in the memory locations. A regular interval can also be referred to as an index frequency, which can be 0.1-10 s, preferably 0.8-1.5 s. The examination frame 72 is set in place on top of the memory 22, when an examination frame 72 with a similar surface area and overall dimensions will contain all the memory locations of the memory 22 inside its index areas 56, 58, and 60. In addition, the examination frame includes a place 77 depicting the base level, which is outside the index areas 56, 58, and 60, and which is not used in the calculation of the indices.

The indices depicting each index area 56, 58, and 60 are preferably compared to the relative conditions of each index and to the absolute values of at least some of the indices. In practice, this means that each index can be compared to an index-specific boundary value and relatively to the values of the other indices. In addition, each index can be monitored from the previous indices of the same index area and the time-dependent development of the index can be monitored.

According to one embodiment, the analysis means 92 are arranged to form classification maps 37 according to FIG. 5 on the basis of the signals, in order to detect biological material. The particle-content data measured by the measuring devices is stored in the memory and an examination frame is placed on top of the memory, when a classification map 37 will be obtained. The index area or areas of the examination frame form at least one index area in the classification map, in this case at least three index areas 56, 58, and 60. The use of at least two and preferably three index areas can reduce the inaccuracy of the method and device and avoid erroneous alarms, as in the method more comparison of the index areas can be created and thus conditions for an alarm. This can be especially important in difficult measuring conditions, in which an air sample can contain, for example, chimney gases, sand, or other impurities.

Hit points for the first index area 56 of less than 1 μm will come particularly from an air sample containing small <1 μm particles, for the second non-fluorescing index area 58 particularly from an air sample containing non-fluorescing, i.e. biologically inert >1 μm particles, and for the third alarm index area 60 from an air sample containing biological particles. The base level accumulating at the hit location 78 is mainly formed of the noise of the photomultiplier tubes and very small (<200 nm) background particles. Particles larger than this are distinguished from background noise and are located in any of the index areas 56, 58, or 60.

In the classification map 37 of FIG. 5, the hit points coming to specific memory locations 76 of the memory 22 are shown relatively on a five-step scale. With the aid of the scale, the memory places, in which there are only a few hit points, can be eliminated, so that the memory places containing most hit points will be more clearly seen. The preselected dimensions of the measurement space can be 10×10-30×30, preferably 15×15-20×20). When using the memory 22, the corresponding dimensions refer to the number of memory locations 76 in the memory 22.

According to one embodiment, the hit points coming to the index area can be recorded in a separate memory from a sliding defined period of time. The length of the period of time can be, for example, 10 minutes. The indices calculated from an index area too can be recorded in a separate memory from a sliding defined period of time. When recording only indices, the amount of data to be stored is considerably smaller than the hit points coming to the index areas during recording. The variables shown in the classification map can be, for example, the fluorescence of the particles and the light scattered by the particles, or the fluorescence of the particles and the arrival of light scattered by the particles and the light scattered by the particles.

Instead of and/or in addition to the directly measured signal values, variables derived from them can be used. An example of such a variable is the correlation (or as another term the cross-correlation) between two signals. This means simply the accumulated value, which is obtained by mutually multiplying the values of these signals and cumulating (or averaging), the result temporally. In that case, at least the second output signal should be such that it does not contain so-called DC components (in other words, the time average value of the signal is zero). The elimination of this DC component can be achieved, for example, by high-pass filtering (which can, in principle, be performed analogously before the AD conversion, or digitally after it), or by removing the mean value form the signal computationally (in other ways). If the correlation is not calculated in real time, the DC component of the signal can be removed afterwards computationally from the accumulated correlation result.

According to one embodiment, the analysis means can be arranged to use the correlations to classify the signals. With the aid of these, various classification maps can be formed, the information provided by which can exploited. These classification maps are formed through the hit points of the measurement space by using general mathematical operations to process the signal. According to another embodiment, the analysis means can also be arranged to use the arrival of the signals, in order to classify the signals.

By means of the analysis means 92 shown in FIG. 2, the defined alarm level is transferred to the alarm and display means 74, which compare the alarm level with preselected criteria. Each criterion can be created from one or several conditions. When the criteria are met, the alarm and display means 74 initiate the alarm procedure. A preselected criterion can also be altered automatically on the basis of real-time measurement information.

The alarm procedure of the device according to the invention can be formed in the manner of the following application example. The alarm and display means examine the indices defined from the recorded data on the basis of at least two periods of time of different length. More specifically, the alarm and display means examine the indices of two different periods of time t from the recorded data, by means of a sliding average value. The first period of time can be measured in seconds, for example 10 seconds, from which time the average value of the indices is examined, which is calculated from the index areas 56, 58, and 60. These indices are marked, for example, with the names (56a), (58a), and (60a), each of which refers to the corresponding index area ((56a) to index area 56 and so on respectively). The second period of time can be measured in minutes, for example 10 minutes, from which time the average value of the indices is also examined, which are calculated from the index areas 56, 58, and 60. These indices are marked, for example, with the names (56*b*), (58*b*), and 60(*b*).

The alarm and display means give a warning, if a predefined condition A is met. The condition A can be, for example, [(60*a*)>(60-*b*)+p], in which p refers in this case to an empirically defined constant. When the condition A is met, the value of the index (60*b*) is frozen. The device then moves to a warning state, where it remains until
  a) the condition A of the warning is no longer valid, when the device returns to the base state,
  b) some exception, i.e. condition B or condition C, is realized, when the values of the indices (56*a*) and (58*b*) are frozen correspondingly, the time duration of the warning is reset when the time window q seconds reopens and the warning state remains, or
  c) the condition A is in force for a specific time, when an alarm is reached.

Here, the condition B can be, for example, [(56*a*)>(56*b*)*s] and condition C can be, for example, [(58*a*)>(58*b*)*v], in which s and v are empirically defined constants.

An alarm takes place, for example, when the warning has be in force without exceptions (condition B or condition C) for a predefined time r. This time can be, for example, 10 seconds. The alarm can be in force until
  a) condition A is no valid, when a return is made to the base state or
  b) some of the exceptions, i.e. condition B or condition C, is realized, when a return is made to the base state.

The conditions can be adjusted as required and in this case changes in the amplification of the measuring means can be exploited. During an alarm, the device can automatically take a sample from the airstream for more accurate analysis.

The alarm algorithms described above can also be used independently, for example, in connection with the alarm of pulse-height method or a corresponding method. The device according to the invention can include software means comprising at least two software timers, in order to determine two periods of time of different length for the examination of the indices.

According to one embodiment, the device can operate in three steps, i.e. by means of the method according to the invention, it monitors an airstream in order to detect biological material, when the alarm level exceeds a preselected criterion it gives an alarm, and it them takes samples from the airstream for more detailed analysis. A databank, which gives precise data on the biological agent after having analysed the substance, can also be added to the device.

Components that wear in use can be minimized in the manufacture of the device, allowing it to operate without supervision and maintenance for long periods of time. The device can be used as a surveillance device installed permanently in buildings, or in a portable form, in which case the device can be used to examine several different areas. Locations where the device can be applied include airports, harbours, railway and metro stations, and similar places, where there are large numbers of people.

The device according to the invention can be modular and other analysers or devices can be connected to it. The control of the device according to the invention can be implemented through an external control unit, or more preferably with the aid of interface software.

The sampling frequencies used by the method according to the invention are very high, so that a considerable number of hit points are created at the index frequency. This means that the calculation of an index formed on the basis of the hit points accumulating in the index areas at the index frequency will require that the analysis means of the device according to the invention have a very large amount of computing power. However, sufficient computing power can be achieved using relatively cheap components.

The basic data of one embodiment of the device according to the invention itemized below. The basic data presented give the basic data of only one example of an embodiment and are not restricted only to them.
  Detection method: UV fluorescence and elastic scattering
  Particle size: 0, 5-10 µm
  Sensitivity: 100 ACPLA
  Response time: <30 seconds
  Air-sample flow 2 l/min
  Light source: CW laser at a wavelength of 405 nm
  Secondary air mixing: Secondary-air mixing
  Compatible components: Disposable 37-mm filters, such as expendable PTFE and gelatine filters
  Data connection: RS-232, RS-485, Ethernet, USB
  Power: Input 85-264 VAC, 9-36 VDC
  Power consumption: 50 W
  Atmospheric humidity range: 0%-90% (unsealed)
  Temperature range:
    Operation: −35-+50° C.
    Storage: −40-+70° C.
  Environmental requirements: Designed to conform to MIL-STD-810 F and MIL-STD-4-61 F
  Size: 57 cm×44 cm×19, 5 cm (H×W×D)

The invention claimed is:

1. Method for detecting biological material in an airstream, which airstream contains particles of biological material and biologically inert material, in which method
  the airstream is fed with the aid of sampling devices into a chamber and out of the chamber after sampling,
  a light beam is emitted towards the airstream by a light source, in order to excite the particles in the airstream, in order to create fluorescence,
  the fluorescence emitted by each particle struck by the light beam is measured with the aid of first measuring means and a fluorescence signal depicting the fluorescence is created,
  the scattered light from each particle struck by the light beam is measured with the aid of second measuring means and a scattering signal depicting the scattering of the light is created,
  the fluorescence signal and the scattering signal are converted into discrete values at the sampling frequency, and
  the discrete values are recorded cumulatively as hit points in an at least 2-dimensional measurement space equipped with selected dimensions,
  an alarm value, showing the presence of a selected biological material, is defined by using a preselected criterion, characterized in that, in the method
  said fluorescence signal is created from emission measured from one or more particles being simultaneously in the chamber,
  said scattering signal is created from scattered light measured from one or more particles being simultaneously in the chamber,
  at least one index area is preselected from the said measurement space,
  a cumulative index is calculated at an index frequency from the hit points accumulated on the each preselected index area, the device is arranged to sample the fluorescence signal and scattering signal continuously, the sampling frequency is 100 kHz-2 MHz.

2. Method according to claim 1, characterized in that there are at least two index areas.

3. Method according to claim 1, characterized in that the indices are compared to relative conditions between each index and absolute conditions for at least some of the indices, on the basis of which, when the conditions are met, an alarm is given.

4. Method according to claim 1, characterized in that the said index frequency is 0.1-10 s.

5. Method according to claim 1, characterized in that, in the at least 2-dimensional memory, the dimensions are the fluorescence of the particles and the light scattered by the particles.

6. Method according to claim 1, characterized in that, in the at least 2-dimensional memory, the dimensions are the light scattered by the particles and the product of the fluorescence of the particles and the light scattered by the particles.

7. Method according to claim 1, characterized in that the correlations of the discrete values are used for calculating the indices.

8. Method according to claim 1, characterized in that the analysis means form classifications maps on the basis of the fluorescence signal and the scattering signal for detecting biological material.

9. Method according to claim 1, characterized in that the alarm is given in three steps, as the following stages biological material is detected in the airstream, when the alarm value exceeds the preselected criterion, the alarm and display means give an alarm, and samples are taken from the airstream for more detailed analysis.

10. Method according to claim 1, characterized in that the alarm and display means compare the said alarm value with the said conditions, which conditions comprise the examination of indices defined from at least two periods of time of different length.

11. Device for detecting a biological material from air, which contains particles of biological material and inert biological material, which device includes sampling means for feeding an airstream into a chamber and for leading the airstream out of the chamber after sampling, a light source directed at the airstream, arranged to emit a beam in order to excite the particles in the airstream in order to create fluorescence, first measuring means for measuring the fluorescence emitted by the particles struck by the beam coming from the light source and for creating a fluorescence signal depicting the fluorescence, second measuring means for measuring the light scattered by the particles and for creating a scattering signal depicting the scattered light, at least one AD converter, for sampling the fluorescence signal and the scattering signal as discrete values at the sampling frequency, analysis means for detecting biological material, classification means and a memory, of which the classification means are arranged to record the said discrete values cumulatively as hit points in an at least 2-dimensional memory equipped with selected dimensions, and in which device characterized in that said first measuring means are arranged to create the fluorescence signal from emission measured from one or more particles being simultaneously in the chamber, said second measuring means are arranged to create the scattering signal from light scatter measured from one or more particles being simultaneously in the chamber, the analysis means are arranged to calculate at the sampling frequency an index of the accumulated hit points for each preselected index area of the memory, from which said indices the analysis means are arranged to define, using a preselected criterion, an alarm level showing the presence of a selected biological material, the device is arranged to sample the fluorescence signal and scattering signal continuously, the sampling frequency is 100 kHz-2 MHz.

12. Device according to claim 11, characterized in that the said selected dimensions are 10×10-30×30.

13. Device according to claim 11, characterized in that the device further includes alarm and display means for giving an alarm on the basis of the said alarm value.

14. Device according to claim 11, characterized in that the device includes software means comprising at least two software timers for determining the two periods of time of different lengths for the examination of the indices.

* * * * *